United States Patent
Poulsen et al.

(10) Patent No.: US 11,474,034 B2
(45) Date of Patent: Oct. 18, 2022

(54) LATERAL FLOW TEST SYSTEM

(71) Applicant: Zoetis Services LLC, Parsippany, NJ (US)

(72) Inventors: Carl Esben Poulsen, Hvidovre (DK); Johan Eriksen, Birkerod (DK); Martin Heller, Farum (DK); Niels Kristian Bau-Madsen, Hellerup (DK)

(73) Assignee: Zoetis Services LLC, Parsippany, NJ (US)

( * ) Notice: Subject to any disclaimer, the term of this patent is extended or adjusted under 35 U.S.C. 154(b) by 130 days.

(21) Appl. No.: 15/916,363

(22) Filed: Mar. 9, 2018

(65) Prior Publication Data

US 2018/0259449 A1    Sep. 13, 2018

Related U.S. Application Data

(60) Provisional application No. 62/470,459, filed on Mar. 13, 2017.

(51) Int. Cl.
*G01N 21/47* (2006.01)
*G01N 21/64* (2006.01)
(Continued)

(52) U.S. Cl.
CPC ..... *G01N 21/4738* (2013.01); *G01N 21/6408* (2013.01); *G01N 21/8483* (2013.01);
(Continued)

(58) Field of Classification Search
None
See application file for complete search history.

(56) References Cited

U.S. PATENT DOCUMENTS

| 5,408,535 A | 4/1995 | Howard, III et al. |
| 7,267,799 B1 | 9/2007 | Borich et al. |

(Continued)

FOREIGN PATENT DOCUMENTS

| CN | 102279263 | 12/2011 |
| CN | 103364547 | 10/2013 |

(Continued)

OTHER PUBLICATIONS

Search Report ROC (Taiwan) Patent Application No. 107108246, Filing Date Mar. 12, 2018.

(Continued)

*Primary Examiner* — Matthew D Krcha
(74) *Attorney, Agent, or Firm* — Scott C. Mayhew

(57) ABSTRACT

A lateral flow test system having an optical reader, a lateral flow cartridge and a computer system is provided. The lateral flow cartridge includes a porous test strip with a reading window into the porous test strip exposing an exposed zone of the porous strip. The optical reader has a reader housing and a slot for inserting the cartridge into the reader housing. The optical reader has an illumination arrangement adapted for illuminating the exposed zone of the porous strip when the cartridge is inserted into the slot. The optical reader further has a video camera configured for acquiring a series of digital images comprising the exposed zone of the porous strip. The computer system receives sets of pixel data representing the plurality of consecutive digital images and calculates wetting progress along the length of the exposed zone of the porous strip based on the sets of pixels data.

16 Claims, 13 Drawing Sheets

(51) Int. Cl.
*G01N 21/84* (2006.01)
*G01N 33/558* (2006.01)

(52) U.S. Cl.
CPC ............. *B01L 2200/0621* (2013.01); *B01L 2300/0825* (2013.01); *G01N 33/558* (2013.01)

(56) References Cited

U.S. PATENT DOCUMENTS

| | | | |
|---|---|---|---|
| 2001/0034068 A1 | 10/2001 | Spivey et al. | |
| 2003/0111602 A1* | 6/2003 | Sato | G01N 23/22 250/310 |
| 2004/0018576 A1* | 1/2004 | DeMatteo | G01N 33/558 435/7.93 |
| 2004/0087033 A1* | 5/2004 | Schembri | B01J 19/0046 506/39 |
| 2004/0096854 A1* | 5/2004 | Choong | G01N 21/6452 435/6.11 |
| 2005/0036148 A1 | 2/2005 | Phelan | |
| 2005/0221502 A1* | 10/2005 | Shindelman | G01N 33/558 436/514 |
| 2010/0177930 A1* | 7/2010 | Dylewski | G01F 1/7086 382/103 |
| 2013/0161190 A1 | 6/2013 | Ewart et al. | |
| 2013/0162981 A1* | 6/2013 | Emeric | G01N 33/48 356/72 |
| 2013/0203627 A1 | 8/2013 | Moll et al. | |
| 2016/0370366 A1 | 12/2016 | Fleming et al. | |

FOREIGN PATENT DOCUMENTS

| | | |
|---|---|---|
| CN | 104081207 B | 10/2016 |
| JP | H07190940 A2 | 7/1995 |
| JP | 2004-170217 A2 | 6/2004 |
| JP | 2013-160550 | 8/2013 |
| JP | 2013160550 | 8/2013 |
| KR | 10-2000-0036176 | 6/2000 |
| KR | 10-2015-0053544 | 5/2015 |
| TW | I340829 | 4/2011 |
| WO | WO 2012/057471 A2 | 5/2012 |
| WO | WO 2015/016960 A1 | 2/2015 |
| WO | WO 2015/022318 A1 | 2/2015 |
| WO | WO-2015022318 A1 * | 2/2015 ........... G01N 33/743 |

OTHER PUBLICATIONS

Office Action of the Intellectual Property Office (Translation) Taiwan Patent Application No. 107108246, Receipt Date Oct. 11, 2018.
PCT International Search Report and Written Opinion, International Application No. PCT/US2018/021663, International filing date Mar. 9, 2018, dated Jun. 28, 2018.
Danish Patent and Trademark Office Search Report, Danish Patent Application No. PA 2017 70177, Date of completion of search report Sep. 6, 2017.
Tong, H. et al., 2004, "Blur Detection for Digital Images Using Wavelet Transform", https://www.cs.cmu.edu/~htong/pdf/ICME04_tong.pdf.
Korean Intellectual Property Office (KIPO) Notice of Preliminary Rejection (English Translation) Korean Patent Application No. 10-2019-7029773, Receipt Date Sep. 22, 2020.
Japanese Patent Office, Japanese Patent Application No. 2019-550722, Notice of Reasons for Rejection (Non-English), Dispatch Date: Jan. 5, 2022.
Japanese Patent Office, Japanese Patent Application No. 2019-550722, Notice of Reasons for Rejection (English Translation), Dispatch Date: Jan. 5, 2022.
China National Intellectual Property Administration, China Patent Application No. 201880017956.9 First Office Action and Search Report (English Translation), dated Jul. 5, 2021.

* cited by examiner

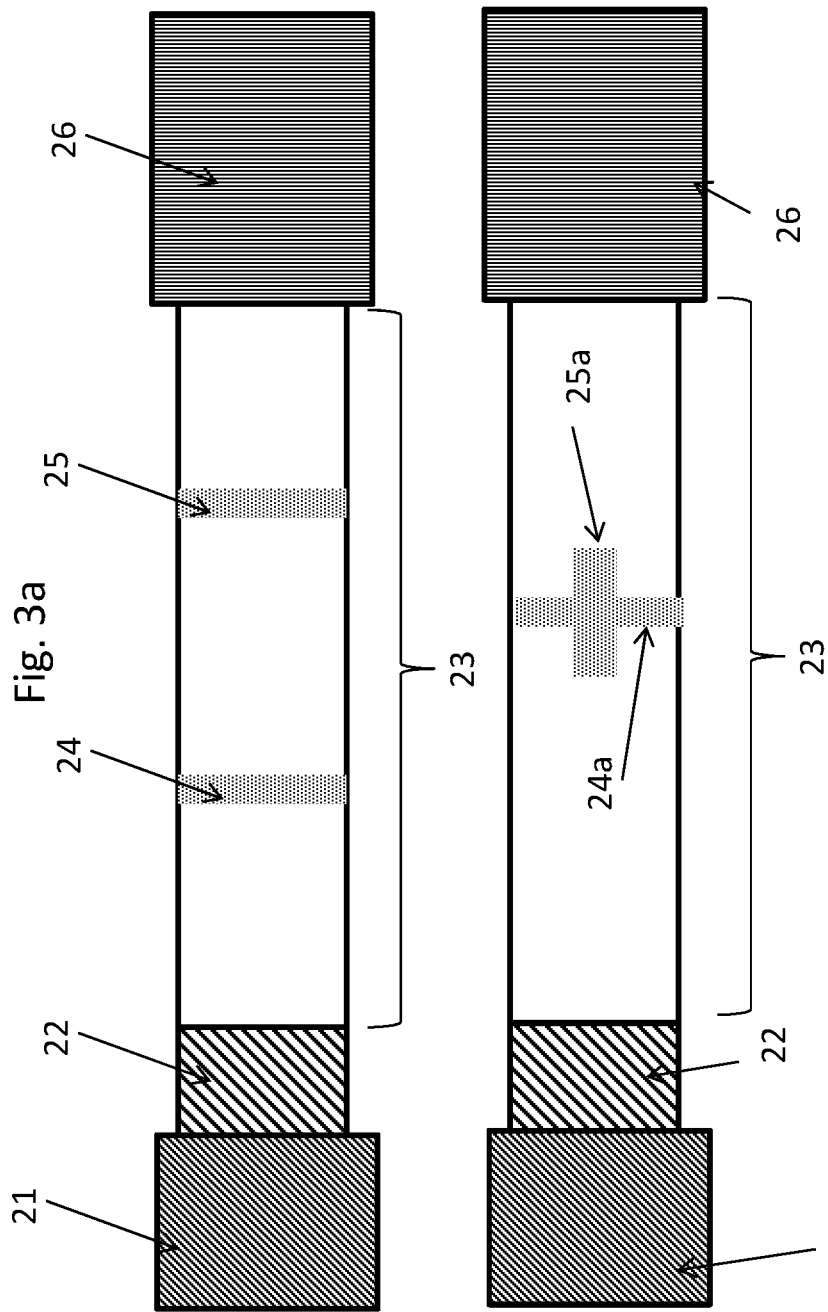

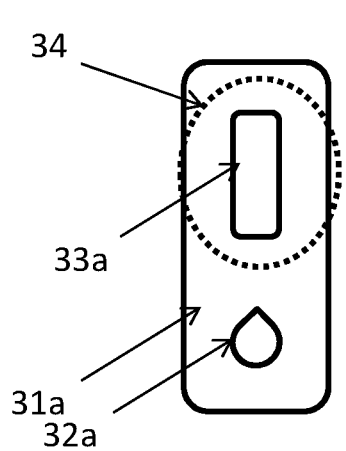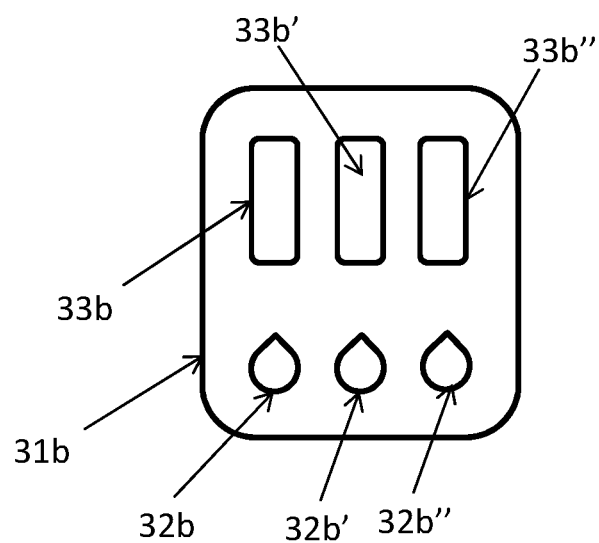
Fig. 4a
Fig. 4b

LATERAL FLOW TEST SYSTEM

CROSS REFERENCE TO RELATED APPLICATION

This application claims the benefit of U.S. Provisional Patent Application No. 62/470,459, filed Mar. 13, 2017, which is expressly incorporated herein by reference in its entirety.

TECHNICAL FIELD

The present disclosure relates to a lateral flow test reader system comprising an optical reader and a lateral flow cartridge.

BACKGROUND

For many years lateral flow tests have been widely used especially for diagnostic purposes both within human diagnostics and animal diagnostics. Generally lateral flow tests are relatively fast and simple to use. Typically, lateral flow tests are used for medical diagnostics either for home testing, point of care testing, or laboratory use. A widely spread and well known application is the home pregnancy test.

A lateral flow cartridge usually comprises a porous test strip, e.g. of paper, polymer or combinations thereof. The lateral flow cartridge comprises a sampling zone for applying a liquid sample to the test strip. Usually the sampling zone comprises a pad or a pad with a fluid reservoir, such that a sufficient amount of fluid can be applied, while at the same time the risk of flooding the strip is low. After application of a liquid sample to the sampling zone, the liquid sample migrates along the length of the test strip. The test strip usually comprises a test mark zone and a control mark zone arranged in the mentioned order relative to the migration propagation of the fluid. The test mark zone changes light response (e.g. color or emission upon excitation) upon positive detection of a selected target molecule (analyte) in the fluid sample and the control mark zone changes light response upon being wetted by the liquid flowing along the strip.

The test strip may e.g. comprise a conjugate zone comprising a dried format of bio-active particles e.g. in a salt-sugar matrix that has the purpose of optimizing chemical reaction between the analyte (e.g., an antigen) and its chemical partner (e.g., antibody) that has been immobilized on the particle's surface. The sample fluid dissolves the particles and flow further along the strip while being mixed with the dissolved particles and optional analyte binds to the particles. The test mark zone comprises immobilized capture molecules configured for capturing conjugates of particles and analytes (or the analyte as such). As the sample fluid reaches the test mark zone the (optional) analyte-particle is captured and thus accumulates in the test mark zone. Due to a marker of the particle the test mark zone changes light response. The change of light response is often a change of color, but it may also be a change of light emission upon excitation e.g. where the particle comprises Q-dots and/or a change of fluorescence.

As the sample fluid reaches the control mark zone the particles are captured by immobilized capture molecules raised against the particles (often against the antigen of the particles) and it can be verified that the test has been completed.

Whereas a lateral flow cartridge may be visually read out it is generally preferred to read out the lateral flow cartridge by an optical reader that can read the test mark zone and the control mark zone. In recent years a lot of different test readers for reading out a lateral flow cartridge have been brought on the market including both stationary and hand held readers. Many of these readers have focused on providing accurate read out and on making the readers small for point of care use.

However, for many readings the resulting read out of the test mark zone and the control mark zone may not provide the full result. Thus, it has been found that there may be many errors that are caused by incorrect sampling of the liquid sample, over sampling (adding too much liquid), misplaced pad in the wetting zone, or fault migration of the liquid sample e.g. by migration in local branches e.g. circumventing the area comprising the bio-active particles.

US2005036148 describes an assay result device for reading the result of an assay performed using a liquid transport carrier, the device comprising: at least one light source capable of emitting light incident upon at least one of two or more spatially separated zones of the carrier; a photodetector so positioned as to be capable of detecting light emanating from each of the two zones and generating signals representing the presence or absence of a fluid sample in the respective zone; and a computation circuit responsive to the signals to: calculate a flow rate for a fluid flowing along the carrier; compare the calculated flow rate to upper and lower limits; and reject the assay result if the calculated flow rate is outside the upper and lower limits. Thereby the reader device may determine the flow rate of the fluid.

BRIEF SUMMARY

The above and other needs are met by aspects of the present disclosure which, according to one aspect, provides a lateral flow test system comprising an optical reader, a lateral flow cartridge and a computer system, the lateral flow cartridge has a proximal portion and a distal portion and comprises a porous test strip comprising and/or in contact with a sampling zone and with a strip length and a cartridge housing supporting said porous test strip, wherein said cartridge housing has an inlet opening for applying liquid to the sampling zone and at least one reading window into the porous test strip at its distal portion exposing at least an exposed zone of said porous strip, having a length and a width, said exposed zone comprises at least a portion distally to the sampling zone. The optical reader comprises a reader housing and a slot for inserting at least the distal portion of the cartridge into said reader housing, said optical reader further comprises an illumination arrangement adapted for illuminating said at least one exposed zone of said porous strip when said cartridge is inserted into the slot of the reader housing and a video camera configured for acquiring a series of digital images comprising said exposed zone of said porous strip, wherein the reader is configured for transmitting each digital image as a set of pixel data. The computer system comprises a storing medium and a processor, said processor being configured for receiving said sets of pixel data representing said plurality of consecutive digital images and for calculating wetting progress along the length of said exposed zone of said porous strip based on said sets of pixels data.

Thus, various aspects of the present disclosure provide advantages, as otherwise detailed herein.

BRIEF DESCRIPTION OF THE DRAWINGS

Figure 1:
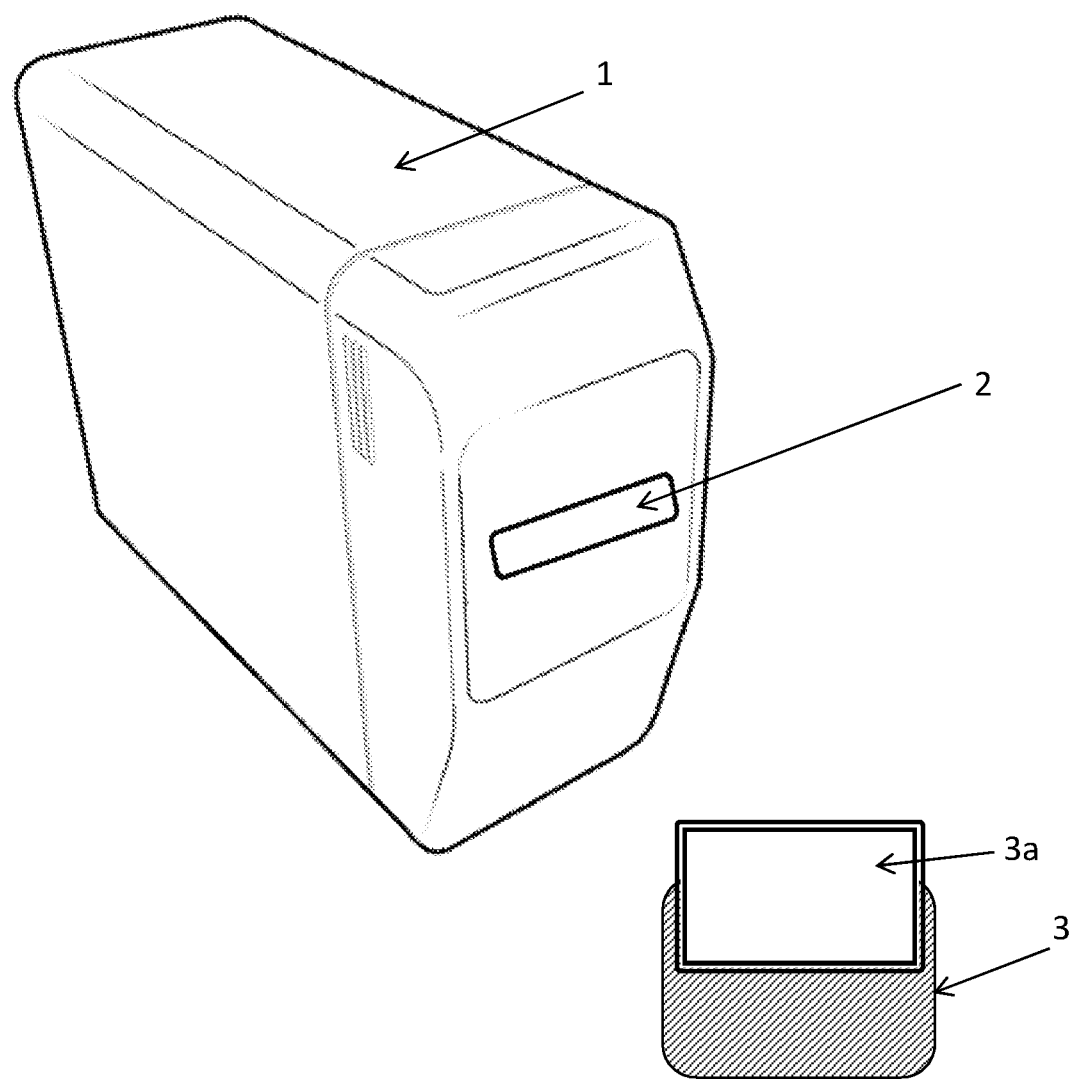
Figure 2:
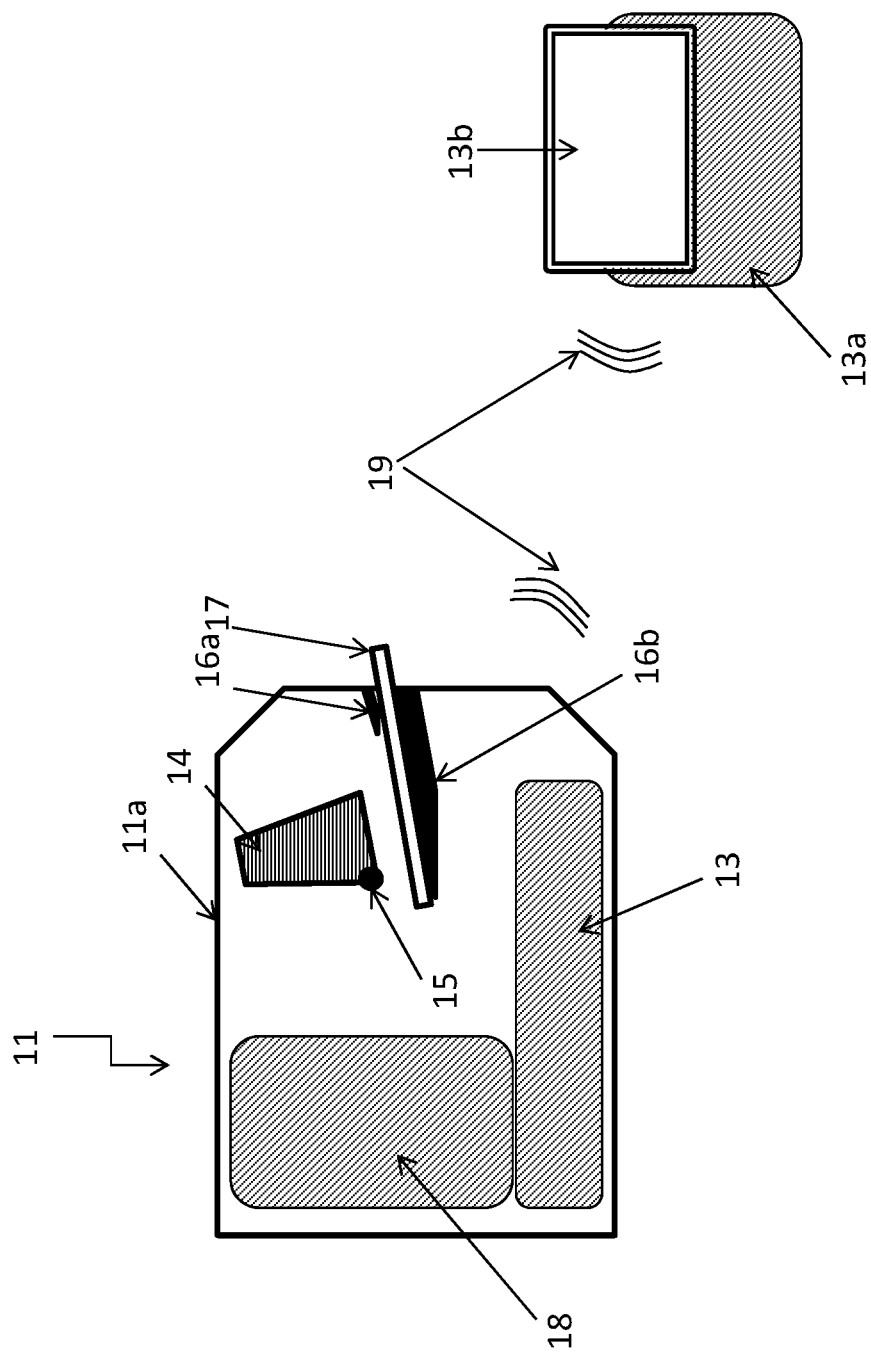
Figure 4C:
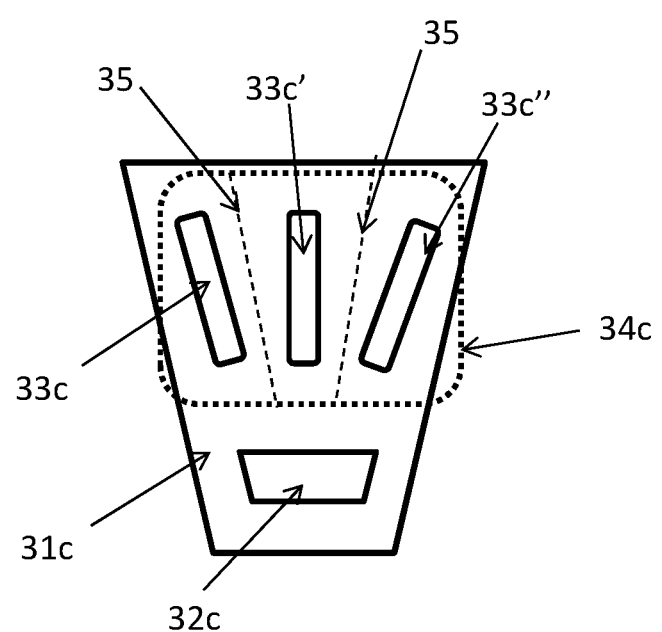
Figure 5:
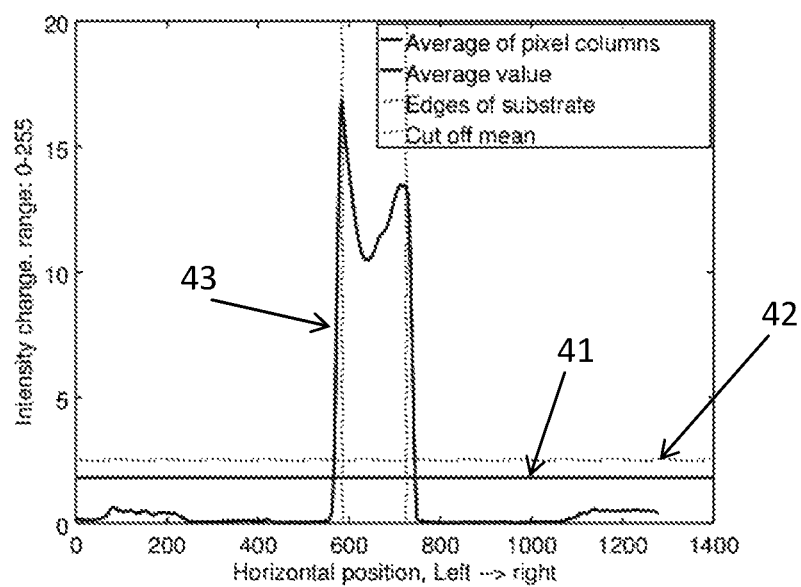
Figure 6:
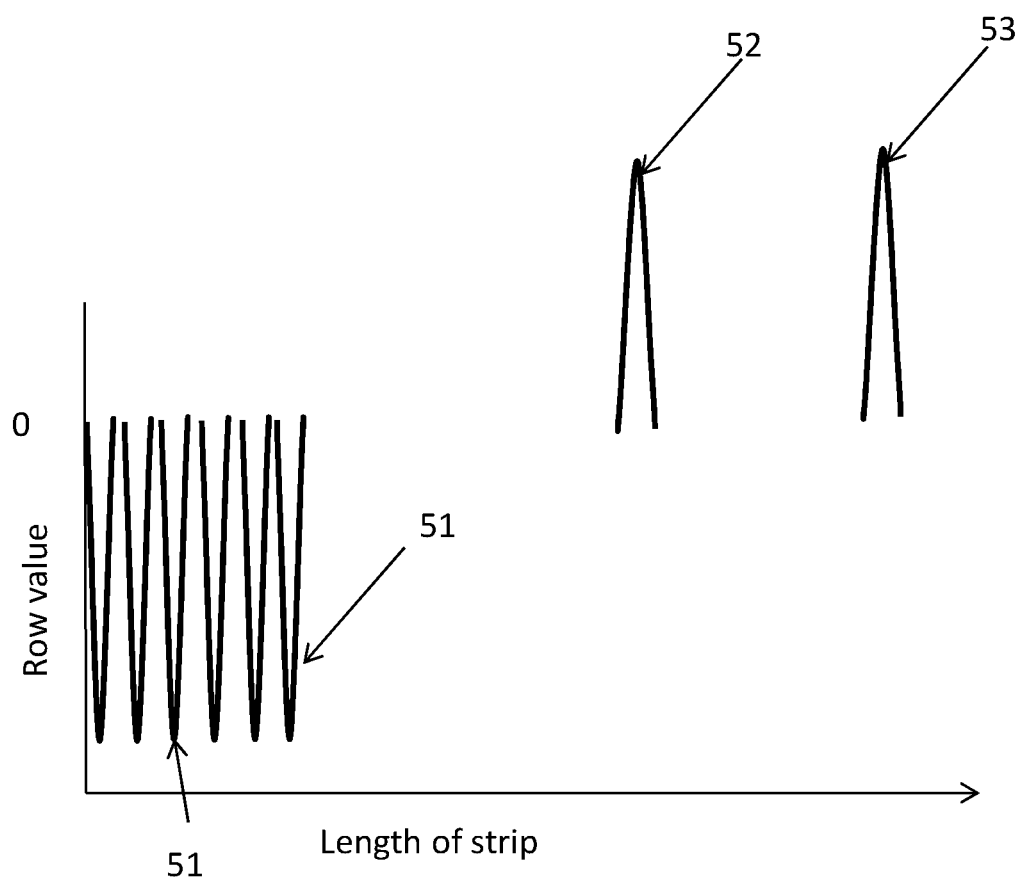
Figure 7:
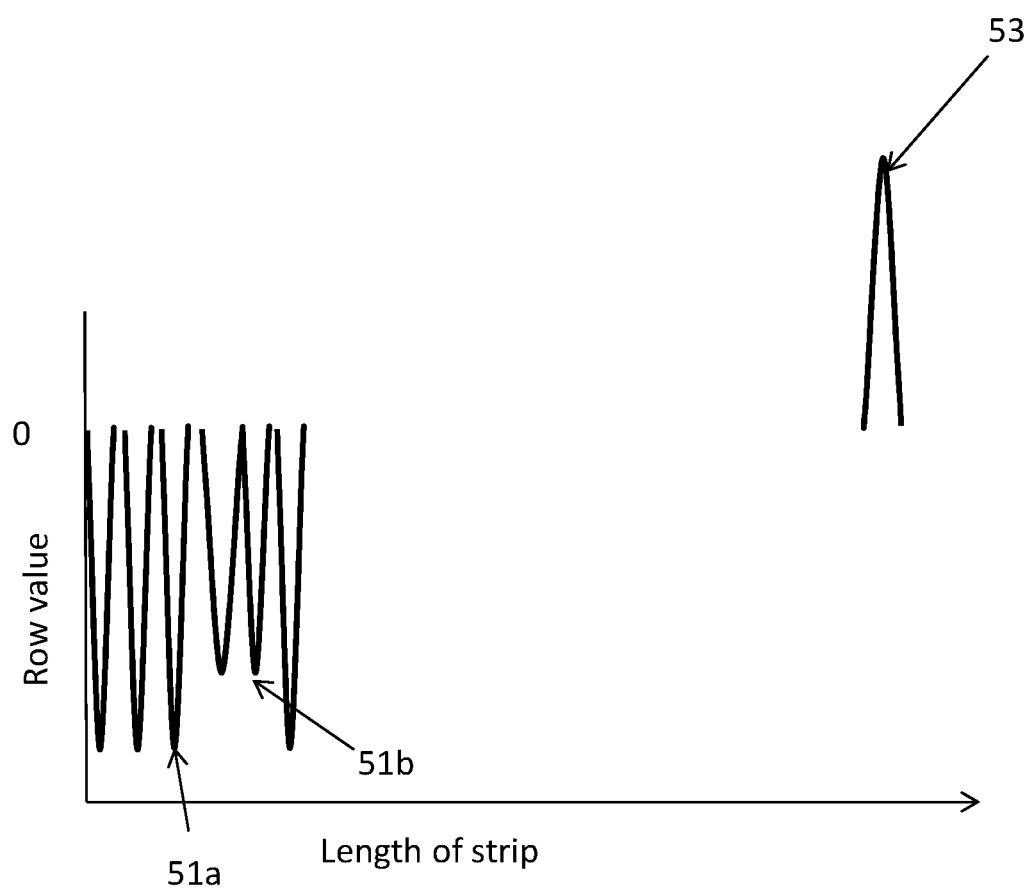
Figure 8:
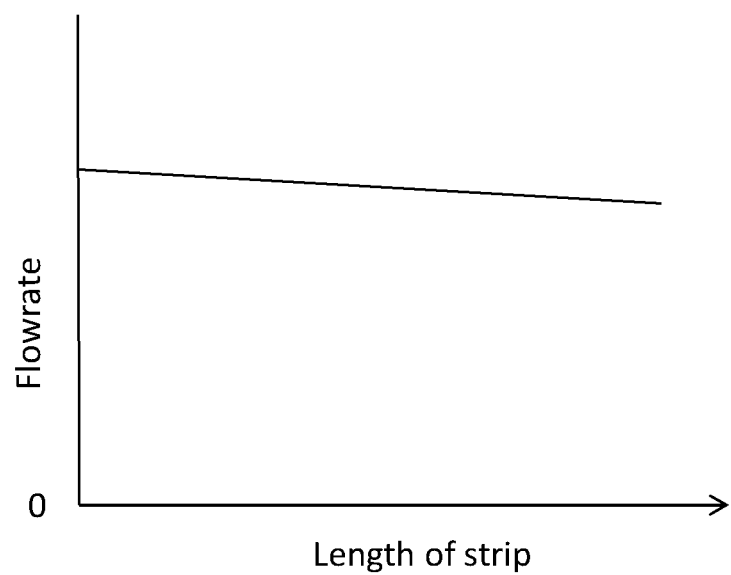
Figure 9:
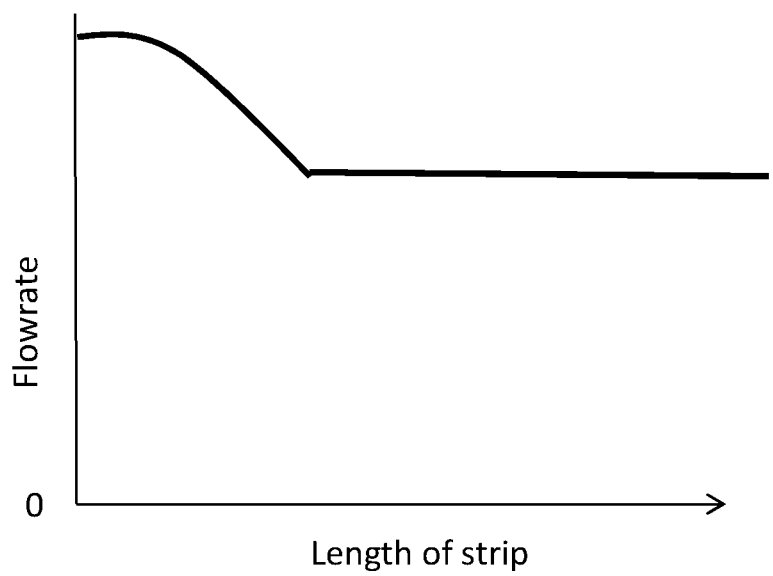
Figure 10:
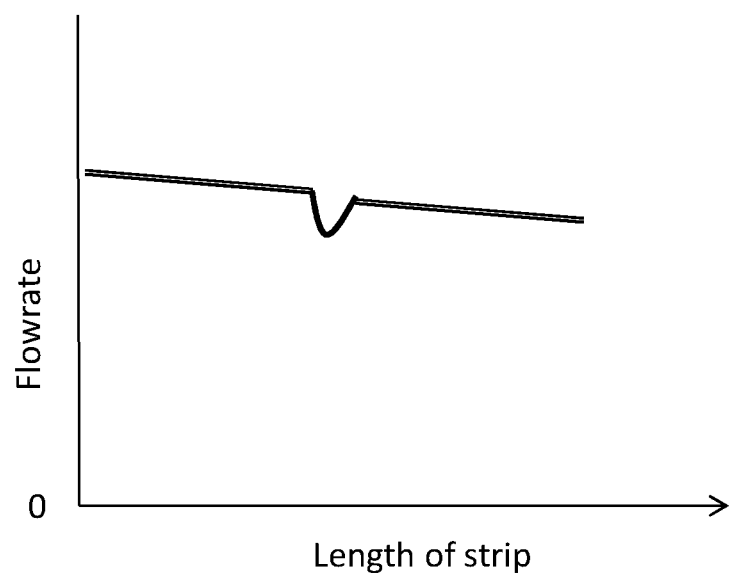
Figure 11:
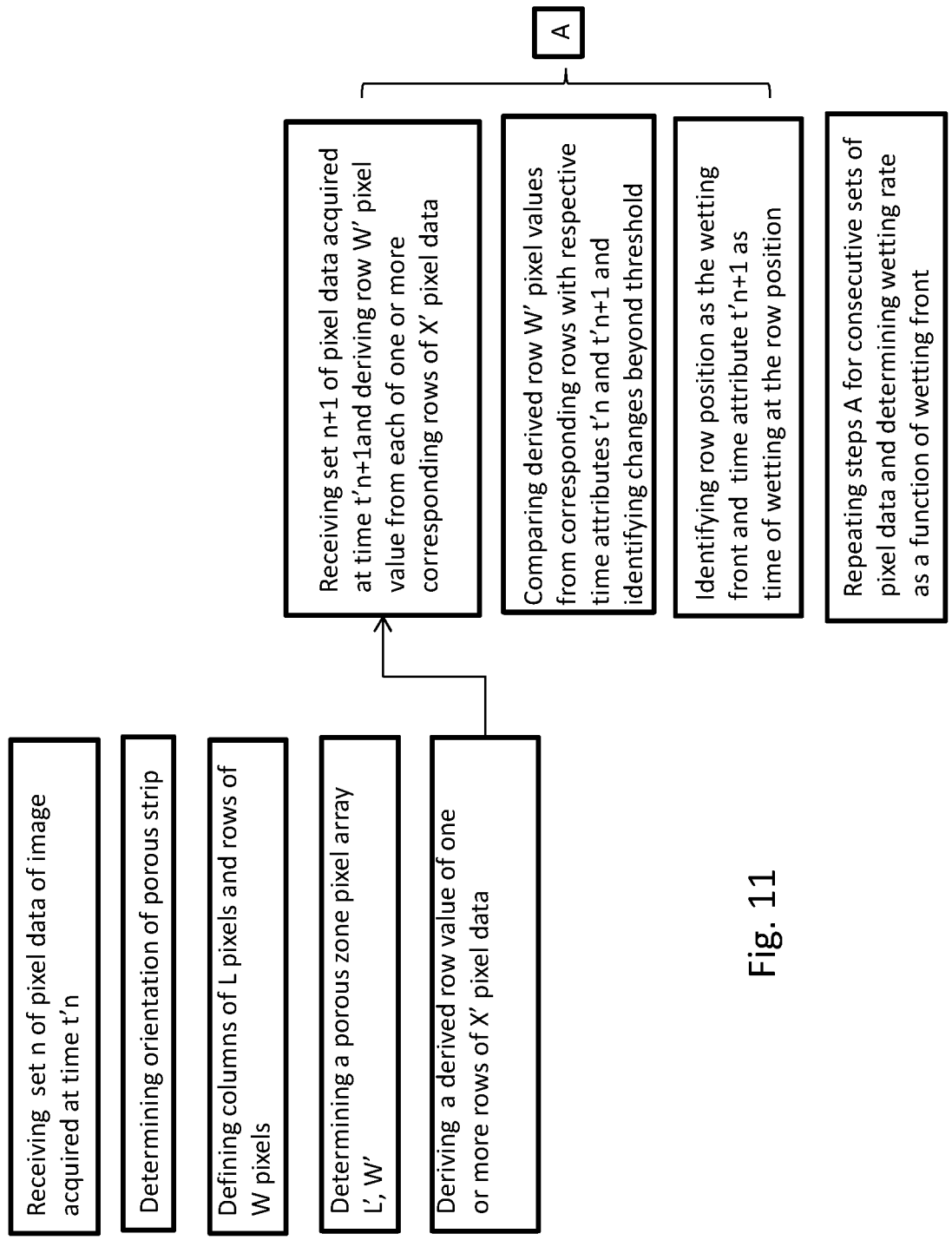
Figure 12:
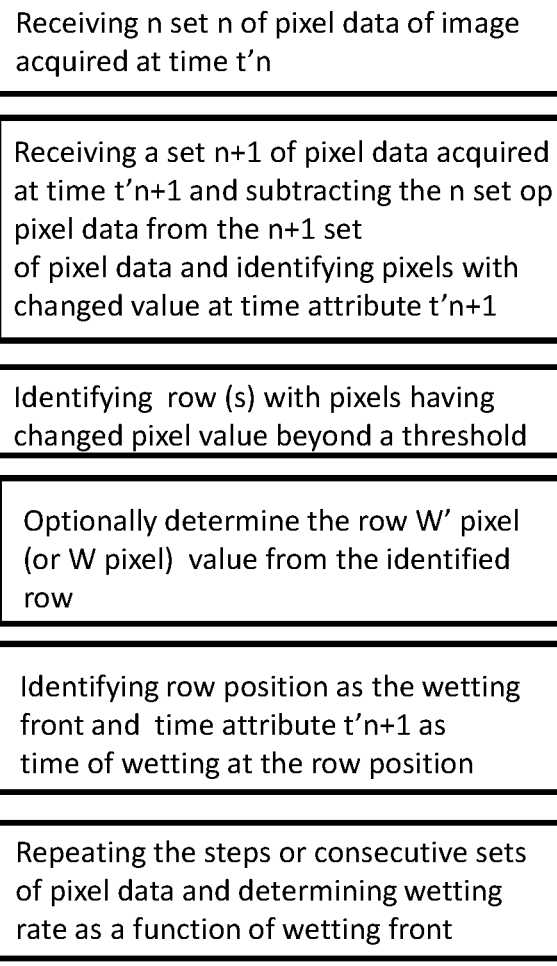

Having thus described various aspects of the present disclosure in general terms, reference will now be made to the accompanying drawings, which are not necessarily drawn to scale, and wherein:

FIG. 1 is a schematic perspective view of an aspect of the lateral flow test system of the present disclosure;

FIG. 2 is a schematic illustration of an aspect of the lateral flow test system of the present disclosure;

FIGS. 3a and 3b illustrate examples of porous test strips suitable for a lateral flow cartridge of an aspect of the present disclosure;

FIGS. 4a, 4b and 4c illustrate examples of lateral flow cartridges suitable for an aspect of the lateral flow test system of the present disclosure;

FIG. 5 is a plot of average values of column of a set of pixel data as a function of the position of the column along the horizontal position aligned with the width of the porous test strip and comprising the exposed zone;

FIG. 6 is a plot of determined row 'W pixel value changes from respective sets of pixel data where the pixel values of the previous set of pixel data have been subtracted from the pixel values of these respective sets of pixel data;

FIG. 7 is another plot of determined row 'W pixel value changes from respective sets of pixel data where the pixel values of the previous set of pixel data have been subtracted from the pixel values of these respective sets of pixel data;

FIG. 8 is a plot of an example of a determined flow rate as a function of the length position of the porous test strip in the exposed zone;

FIG. 9 is a plot of another example of a determined flow rate as a function of the length position of the porous test strip in the exposed zone;

FIG. 10 is a plot of yet another example of a determined flow rate as a function of the length position of the porous test strip in the exposed zone;

FIG. 11 is a process diagram of a computing process of an aspect of a lateral flow test system of the present disclosure; and FIG. 12 is a process diagram of another computing process of an aspect of a lateral flow test system of the present disclosure.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

An object of the present disclosure is to provide a lateral flow test system comprising an optical reader and a lateral flow cartridge which system provides a very accurate read out and with a high capability of validating a lateral flow cartridge test run.

In an aspect it is an object to provide a lateral flow test system capable of detecting if an error in a lateral flow cartridge test run has occurred or is occurring.

In an aspect it is an object to provide a lateral flow test system capable of detecting if a fault migration of a liquid sample in the a lateral flow cartridge has occurred or is occurring.

In an aspect of the disclosure it is an object to provide a lateral flow test system which alleviates at least one of the problems discussed above in a simple and economical feasible way and with a high accuracy and liability.

These and other objects have been solved as described in the present disclosure as defined in the claims and as disclosed herein below.

The lateral flow test system of an aspect of the disclosure comprises an optical reader, a lateral flow cartridge and a computer system.

The lateral flow cartridge has a proximal portion and a distal portion and comprises a porous test strip comprising and/or in contact with a sampling zone. The porous test strip has a strip length which is generally defined as the direction that fluid will progress upon application to the sampling zone. The lateral flow cartridge comprises a cartridge housing supporting the porous test strip. The cartridge housing has an inlet opening for applying liquid to the sampling zone. The cartridge housing has at least one reading window into the porous test strip at its distal portion exposing at least an exposed zone of the porous strip. The exposed zone has a length and a width (also referred to as the vertical length and horizontal width, where the terms "vertical and horizontal are used as relative terms). The length direction of the exposed zone is defined as the propagation direction in the exposed zone of the porous test strip of a fluid applied to the sampling zone. The exposed zone comprises at least a portion of the porous test strip distally positioned relative to the sampling zone.

Such lateral flow cartridges are generally known and in principle any such lateral flow cartridges may be applied in the system. Further preferred lateral flow cartridges are described below.

The optical reader comprises a reader housing and a slot for inserting at least the distal portion of the cartridge into the reader housing. The optical reader further comprises an illumination arrangement adapted for illuminating the at least one exposed zone of the porous test strip when the cartridge is inserted into the slot of the reader housing and a video camera configured for acquiring a series of digital images (also referred to as frames) comprising the exposed zone of the porous test strip. The optical reader is configured for transmitting each digital image as a set of pixel data. Advantageously the video camera of the reader is transmitting the sets of pixel data to the computer system.

The phrase "a set of pixel data" is herein used to mean a plurality of pixel data having identical time attribute. A set of pixel data is preferably data of respective pixels of a single digital image acquired by the video camera.

The computer system comprises a storing medium and a processor, the processor being configured for receiving the sets of pixel data of the plurality of consecutive digital images and for calculating the wetting progress along the length of the exposed zone of the porous strip based on the sets of pixels data. The computer system is preferably configured for storing the sets of pixel data on the storing medium.

It has been found that the lateral flow test system of the present disclosure provides a very accurate determination of the wetting progress of the porous test strip and at the same time reveals if an error in a lateral flow cartridge test run has occurred or is occurring. The progress of the wetting front may be followed to ensure that the porous test strip is wetted in its entire width, without undesired by-pass flow bypassing a part of the porous test strip.

Thus, any fault migration of a liquid sample in a lateral flow cartridge may be observed immediately and the test may be terminated and discarded or alternatively the result may be adjusted if only a minor part of the porous test strip was bypassed. Thereby the user may save time and at the same time obtain a very accurate and reliable result.

The lateral flow test system thereby provides a valuable validating tool for validating a lateral flow cartridge test run.

Further the lateral flow test system also provides a validating tool for validating a batch of lateral flow cartridges. Usually lateral flow cartridges are produced in batches of e.g. 10.000 or 1000. The mass production sometimes results in systemic errors. For example the production may comprise that the porous test strip are cut from a band or sheath of porous material and the chemicals for the tests may be deposited onto the sporous material before or after cutting the test strips and the strips are there after mounted in housings.

It happens that the deposition of the chemicals is not entirely correct in amount and/or position and/or the porous material may have deformations or other material faults that may impact the migration of fluid in the porous material.

Thus, sometimes many items of a batch of a lateral flow cartridge may have faults and thus by validating a few lateral flow cartridges from a batch using an embodiment of a lateral flow test system of the present disclosure any systemic fault may easily be discovered.

Thus the lateral flow test system has been found to be very valuable for validating test runs and at the same time save time both because faults may be discovered very early in a test run and also due to the fact that the number of test runs may be reduced since the validation of the test runs ensures that practically all validated and approved test runs may be highly reliable.

The phrase "test run" is used herein mean the performing of a lateral flow test comprising applying a sample fluid to the sampling zone of a lateral flow cartridge and observing the wetting progress in the exposed zone.

The term "substantially" should herein be taken to mean that ordinary product variances and tolerances are comprised.

The term "about" is generally used to include what is within measurement uncertainties. When used in ranges the term "about" should herein be taken to mean that what is within measurement uncertainties is included in the range.

The term "liquid sample" or "sample" or "test liquid" means any liquid containing sample including liquid sample comprising solid parts, such as dispersions and suspensions. The sample comprises liquid at the time of performing the method.

Throughout the description or claims, the singular encompasses the plural unless otherwise specified or required by the context.

The terms "test" and "assay" are used interchangeably.

The terms "configured for" or "configured to" are herein used to mean that the item in question is specifically constructed, designed or programmed to perform the purpose in question.

The lateral flow cartridge may in principle be any kind of a lateral flow cartridge adapted to be used with the reader.

The distal portion of the lateral flow cartridge is the portion of the lateral flow cartridge that is within the optical field of the video camera, and the proximal portion of the lateral flow cartridge is the portion which is opposite to the portion to be inserted into the slot of the reader. Usually the lateral portion will not be fully inserted into the reader, but will protrude therefrom for easy inserting and removal from the reader. Advantageously the inlet to the sampling zone will be at the proximal portion of the lateral flow cartridge. In an embodiment the inlet to the sampling zone will be at the proximal portion of the lateral flow cartridge at a position protruding out from the reader when the lateral flow cartridge is fully inserted. Thereby the fluid sample may be added to the sampling zone after the lateral flow cartridge has been fully inserted into the reader. Alternatively the fluid sample may be added to the sampling zone before inserting the lateral flow cartridge into the slot of the reader or while the lateral flow cartridge is partly inserted into the slot of the reader.

The porous test strip may be any kind of porous test strip such as the types usually applied for lateral flow test strips. The porous test strip may be in one piece or it may comprise two or more sections which are in contact for the migration of fluid. In the prior art a large number of test strips for lateral flow tests are known and the porous test strip may in an embodiment be selected from such known test strips. In an embodiment the porous test strip comprises from its proximal end towards its distal end a sampling pad arranged to be at the sampling zone, a conjugate pad with the labelled particles, a porous membrane (e.g. of nitrocellulose) optionally carrying a test zone and/or a control zone and a fluid sink optionally comprising an adsorbent pad. All the pads and the membrane(s) may for example be applied onto a backing holding the elements in relative position to ensure the migration of wetting of the strip.

The sampling pad may e.g. be of cellulose and/or glass fiber and a sample is applied on this pad to start assay. Its function is to transport the sample liquid downstream towards the conjugate pad. The sampling pad may comprise component(s) or feature(s) for pretreating the liquid sample e.g. for separation of sample components, removal of interferences, adjustment of pH, etc.

The conjugate pad may e.g. be of glass fiber, cellulose, polyesters or mixtures comprising one or more of these fibers and the conjugate pad comprises the labelled particles (conjugates) which are configured for binding to the analyte of interest. Where the assay is a competitive assay the sampling pad or a further pad adjacent to the conjugate pad may carry a competing molecule or particle. The labelled particles are released from the conjugate pad upon contact with the liquid sample and bind to the analyte or a competing molecule/particle.

The inlet opening for applying liquid to the sampling zone may for example be an opening in the cartridge housing. The inlet opening preferably is sufficient for application of a drop of the liquid sample and/or the inlet opening may be shaped to suck the sample into the sampling zone by capillary effects.

The inlet opening and the reading window are usually separate openings into the porous strip to ensure an accurate application of a liquid sample to the sampling zone, however, in one embodiment the inlet opening and the reading window are united e.g. with a narrow ribbon shaped opening connecting the inlet opening and the reading window.

The cartridge housing has the purpose of supporting the porous test strip and preferably the cartridge housing is of a polymer, such as polydimethylsiloxane (PDMS), polycarbonate (PC) or polystyrene (PC). The surface of the cartridge housing surrounding the exposed zone may advantageously have light reflecting properties which differ significantly from the light reflection properties of the porous test strip in respect to the illumination light from the illumination arrangement.

The illumination arrangement may comprise any kind of illuminating light source, such as one or more diodes and/or laser light soured(s). For cost reasons diode(s), such as led(s) are preferred. The illuminating arrangement may advantageously be configured for illuminating the exposed zone of the porous test strip preferably by flash illumination.

The illumination light may have any bandwidth preferably comprising electromagnetic waves of light within 400 nm to 2600 nm, and preferably comprising electromagnetic wavelengths within the visible range of from about 400 nm to about 700 nm, such as from about 500 to about 600 nm.

The video camera may e.g. be a webcam i.e. a video camera that streams its images in real time to a computer—here the computer system. Whereas the term webcam in its original sense means that the camera is connected to the web, the term as used herein means that the camera streams its images in real time to the computer system.

The video camera may include one or more lenses and an image sensor e.g. in the form of a pixel sensor array and support electronics.

Image sensors may e.g. be CMOS or CDD. To ensure suitable sets of pixel data for obtaining a fast and accurate determination of the wetting progress the video camera may be advantageously a 2 dimensional pixel array video camera, preferably, independently of each other, having more than 50, such than more than 100 pixels in each of the 2 dimensions.

The support electronics are configured to read the image from the sensor and transmit it to the computer system.

The video camera may advantageously be held in a fixed position in the reader housing. In an embodiment the video camera is arranged in a fixed position relative to the inserted cartridge.

In an embodiment the video camera may have two or more positions for being adapted for reading different shapes and designs of lateral flow cartridges. During the test run the video camera should advantageously be held in a fixed position.

Advantageously the video camera is configured for operating with a frame rate (image rate) of at least about 0.1 Hz, such as at least about 1 Hz, such as at least about 10 Hz, such as at least about 25 Hz, such as at least about 50 Hz, such as at least about 90 Hz. The desired frame rate depends largely on the test to be performed and the properties—such as wetting properties—of the porous test strip. It has been found that a relatively low frame rate e.g. of 15 Hz or less or even 0.2 Hz or less may for many test runs be sufficient to provide a very accurate determination of the wetting front as the fluid is migrating downstream through the porous test strip.

The velocity (flow rate) of the wetting front may be usually in the range of from about 0.1 to about 0.001 cm per second. The flow rate mainly depends on the porous test strip. Usually the porous strip is several centimeters long, normally about 3-8 cm or longer.

In an embodiment the frame rate may be selected to provide that at least 5, such as at least 10, such as at least 25 or even at least 100 sets of image data are acquired of the of the exposed zone of the porous strip during the time that the wetting front is progressing from a first end of the exposed zone closer to the sampling zine to a second end of the exposed zone further from the sampling zone.

The distance from the first end to the second end of the exposed zone may advantageously be at least about 1 cm, such as at least about 2 cm, such as at least about 3 cm.

In an embodiment, the frame rate may be selected to provide that at least 5, such as at least 10, such as at least 25 or even at least 100 sets of image data are acquired of the of the exposed zone of the porous strip during the time that the wetting front is progressing from the first end of the exposed zone to at least one of a test or a control zone.

The distance from the first end of the exposed zone to at least one of the test or control zone may advantageously be at least about 0.5 cm, such as at least about 1 cm, such as at least about 2 cm, such as at least about 3 cm.

In an embodiment the video camera comprises a pixel sensor array such as a CMOS or a CDD, the pixel sensor array comprises a 2 dimensional array of pixels.

The 2 dimensional array of pixel sensors of the camera is in the following referred to as N×M pixel array. The video camera advantageously comprises a pixel array comprising rows of N pixels and columns of M pixels. For high resolution it is generally desired that the pixel array has a relatively high fill factor, such as a fill factor of at least about 50%, such as at least about 75%.

The fill factor of an image sensor is the ratio of a pixel's light sensitive area to its total area or for pixels without microlenses the fill factor is determined as the ratio of photodiode area to the total pixel area.

The computer system may be a single computer or a group of computers in data communication. In an embodiment the computer system comprises a computer encased in the reader housing. In an embodiment the entire computer system is encased in the reader housing or in a housing connected to the reader housing.

Upon receipt of the sets of pixel data representing the sets of pixel data, the computer system advantageously is configured for storing the received sets of pixel data.

The pixel data comprises at least one value for each pixel. The processor may comprise an algorithm for detecting and correcting defective pixel values e.g. to compensate for noise or sensing defect. In an embodiment the processor is configured for identifying pixel errors and to compensate for such pixel errors by replacing an identified pixel error value by a mean value of adjacent pixels.

The pixel value may be a value representing the total light intensity sensed by a pixel (e.g. number of collected photons). In an embodiment the pixel value represents the intensity of a certain wavelength range (e.g. green light, blue light or red light).

In an embodiment the camera comprises a plurality of photosites wherein each of the photosites may represent a pixel or a group of four photosites represents a pixel. The photosites may e.g. comprise a filter e.g. in the form of a color filter array forming a Bayer array of photosites comprising alternating rows of red-green and green-blue filters. Each group of four pixels may for example form a pixel.

For high resolution it is preferred that the pixel value is a value of the total light intensity of the pixel.

Where the label of the conjugate to be observed at the test zone and/or the control zone has a certain color—e.g. red, the processor may perform separate processing of the pixel value at the test zone and/or the control zone using the intensity of this certain color (red) wavelength range. Thereby the control mark and/or the test mark will be revealed very fast and with high accuracy e.g. both for qualitative determination and optionally also for quantitative determination e.g. to find the concentration of an analyte in a liquid sample.

The processor is configured for processing the sets of pixel data representing the plurality of consecutive digital images and based on changes of pixel values of respective pixels the processor is configured for calculating the wetting progress along the length of the exposed zone of the porous strip. The processor may simultaneously determine if the wetting of the porous test strip is complete in its entire width or if a portion of the porous test strip has been by-passed by the fluid sample.

It has been found that even where the sample is transparent, the light reflecting properties of the porous test strip changes when wetted. Thus, by determining the changes of light reflection from one image to the next the wetting progress along the length of the exposed zone of the porous strip may be monitored by the lateral flow test system with a very high accuracy.

In an embodiment the video camera is arranged relative to the length of the porous test strip, such that its row pixels N and column pixels M are aligned with respectively the width and the length of the porous strip at least in the exposed zone. Thereby the rows of N pixels and columns of M pixels define columns of L pixels aligned with the length of the test strip and rows of N pixels aligned with the width of the test strip. Thus, a column of L pixels represent a line along the length of the test strip and a row of W pixels represents a line orthogonal to the length of the test strip.

In an embodiment it has been found that the computer system may select the columns L and rows W without requiring the pixel array of the camera to be aligned with the width and the length of the porous test strip. In this embodiment the processor is configured for determining the best fit of columns of pixels of the camera pixel array that are aligned along the length of the porous test strip and defining these as columns of L pixels and the processor is configured for determining the best fit of rows of pixels of the camera pixel array that are aligned orthogonal to the length of the porous test strip and defining these as rows of L pixels.

In an embodiment the processor is configured for defining columns of L pixels and rows of W pixels of the pixels sensor array, by a method comprising comparing pixel values of a set of pixel data and determining the orientation of the porous strip relative to the pixel array of the camera and defining columns of L pixels aligned with the length of the strip and rows of W pixels aligned with the width of the strip. This embodiment ensures a good reading even in case the cartridge is moved or not accurately positioned.

The processor may make use of the difference in light reflection properties of the porous test strip relative to the housing surrounding the reading window and by finding adjacent pixels of similar value and adjacent pixels of not-similar values the processor may identify the width of the reading window and thereby the orientation of the porous test strip.

In an embodiment the processor is configured for comparing pixel values of a set of pixel data by a method comprising for each of a plurality of camera pixel rows determining an average or a mean camera row pixel value and determining pixels that have pixels values of at least 10% above or below the camera row pixel value, such as determining pixels that have pixels values of at least 25% above or below the camera row pixel value, such as at least 25%, such as at least 50%, such as at least 100%, such as at least 200% above or below the camera row pixel value.

The processor need not process the pixel values of all the camera pixel rows. For example in an embodiment the processor is configured for determining an average or a mean camera row pixel value for every $5^{th}$ to $20^{th}$ camera pixel rows and from this the processor extrapolates the porous test strip orientation.

In an embodiment the processor is configured for determining first and last pixels of each of the plurality of camera pixel rows which have pixels values of at least 10% above or below the respective average or mean camera row pixel value, such as at least 25%, such as at least 50%, such as at least 90% above or below the respective average or mean camera row pixel value, such as at least 100%, such as at least 200% above the respective average or mean camera row pixel value. The processor is advantageously configured for determining the orientation of the porous strip based on the positions of the determined first and last pixels of each of the plurality of camera pixel rows. The processor will identify the first and last pixels of each of the plurality of camera pixel rows and their positions and where a number of these positions are aligned along a straight or a curved line, this line will be identified as an edge of the porous strip or of the reading window and/or the exposed zone of the porous test strip.

In an embodiment the lateral flow cartridge comprises an alignment fiducial mark having a reflectivity that differs by at least 10%, such as at least 50%, such as at least 100%, such as at least 200% from the reflectivity of the housing surrounding the exposed zone. The processor is configured for determining the pixels of a plurality of camera pixel rows collecting photons reflected from the alignment fiducial mark and based on the positions of the determined pixels collecting photons reflected from the alignment fiducial mark, the processor is configured for determining the orientation of the porous strip. The fiducial mark may advantageously be an asymmetrical mark to provide that the orientation of the lateral flow cartridge relative to the video camera may easily be determined. In an embodiment, the fiducial mark may comprise a line or a line of dots along the edge of the reading zone. The fiducial mark may for example have a color different from the color of the cartridge housing in the area surrounding the reading window and the pixel value applied in the processing may preferably be a pixel value representing the intensity of the color of the fiducial mark, such as red.

It has been found that the processor may be configured for defining columns of L pixels and rows of W pixels from pixel values of one set of pixel data. Alternatively and for increasing accuracy, the processor may be configured for defining columns of L pixels and rows of W pixels from pixel values of two or more sets of pixel data.

Where the computer system comprises data representing the geometry of the lateral flow cartridge including size of the reading window, the processor may be capable of defining columns of L pixels and rows of W pixels with an even higher accuracy and the number of camera pixel rows required for being processed by the processor may be relatively low, such as 5-50 camera pixel rows, such as 10-40 camera pixel rows.

Advantageously the processor is configured for receiving the sets of pixel data of the plurality of consecutive digital images consecutively as the images of the series of digital images are acquired, for example by real time streaming of the data. Thereby a web camera may be used and the camera is not required to temporarily store data.

In an embodiment the processor is configured for receiving the sets of pixel data of the plurality of consecutive digital images in one or more batches of pixel data. This embodiment may provide a reduced rate of errors caused by the transmission of data. This embodiment may be desired for use in validating lateral flow cartridge batches.

In an embodiment each set of pixel data representing an image comprises a pixel value for each of a plurality L*W pixels. The pixel data may comprise sub pixel values for respectively red, blue and green, such as values representing the intensities.

In an embodiment one of these sub-pixel values for each pixel represents the pixel value. In an embodiment the pixel value is a value derived from the sub-pixel values, such as the sum of the sub-pixel values or a weighted sum of the sub-pixel values. For example where it is desired to increase the sensitivity to the red color—e.g. for detecting a red fiducial mark, a red test mark and/or a red control mark—the red color may be weighted higher than the other colors.

Advantageously each set of pixel data is associated with a time attribute representing a time of acquisition of the respective image of the series of images. Thereby the processor may compare pixel values of selected pixels with pixel values of corresponding pixels having different time attributes.

In an embodiment each set of pixel data of the series of frame is associated with a relative time attribute representing a relative time of acquisition of the respective image of the series of images.

In an embodiment each set of pixel data of the series of frame is associated with an actual time attribute representing an actual time of acquisition of the respective image of the series of images.

In an embodiment one or more sets of pixel data of the series of frame are associated with an actual time of acquisition of the respective image of the series of images. Preferably the set of pixel data representing the first frame of a series is associated with an actual time of acquisition. Each of one or more of the remaining sets of pixel data may advantageously be associated with a relative time attribute representing a relative time of acquisition relative to the actual time of acquisition of a previous frame, such as the first frame of a series.

In an embodiment the processor is configured for comparing pixel values of at least one l, w pixel of two or more of sets of pixel data of the series of digital images to determine the time attribute of a set of pixel data where the l, w pixel value data differs relative to l, w pixel values of corresponding pixels from previous or subsequent sets of pixel data. The terms "w, l pixel value" or "l, w pixel value" means the value of the pixel at position l, w/w, l in the coordinate system of rows of W pixel and column of L pixels.

By comparing pixel values of at least one l, w pixel of two or more sets of pixel data of the series of digital images the processor may determine the time that light reflection is changing at a position at the porous test strip corresponding to the l, w pixel (i.e. the position at the porous test strip that has reflected the photons captured by the pixel sensor representing the w, l pixel) due to wetting.

In an embodiment the processor is configured for calculating the average or mean row pixel value of a selected row of W, L aligned pixels for two or more of sets of pixel data of the series of digital images. The phrase a "row of W aligned pixels" is used to mean the defined rows of W pixels aligned with the width of the strip and the phrase "column of L aligned pixels" is used to mean the defined columns of L pixels aligned with the length of the strip.

The processor preferably further is configured for comparing the average or mean row pixel value of the row of W aligned pixels of the respective sets of pixel data to determine the time attribute of a set of pixel data where the mean row pixel value of the row of W aligned pixels differs relatively to the mean row pixel value of the row of W aligned pixels of previous or subsequent sets of pixel data.

In an embodiment the processor is configured for subtracting the respective pixel values of one set of pixel data from the respective pixel values of a previous or a subsequent set of pixel data and determining if any of the pixel values have changed and if so determine the time attribute of the associated to the set of pixel data where the changes have occurred and preferably the pixel position of the changes. The processor may further be configured for correlating the position of the pixel changes to the position at the lateral flow cartridge and in particular the reading zone of the lateral flow cartridge to determine the wetting progress.

The processor may advantageously be configured for subtracting the respective pixel values of one set of pixel data from the respective pixel values of a subsequent set of pixel data and determining if any of the pixel values have changed and if so determine the time attribute of the associated to the set of pixel data where the changes have occurred and the correlated position at the lateral flow cartridge and in particular the reading zone of the lateral flow cartridge. Preferably the processor is configured for in consecutive steps as sets of data are received, subtracting the respective pixel values of a previous set of pixel data from the respective pixel values of a subsequent—preferably most recently received set of pixel data and determining if any of the pixel values have changed and if so determine the time attribute of the associated to the subsequent or most recent set of pixel data where the changes have occurred and the correlated position at the lateral flow cartridge and in particular the reading zone of the lateral flow cartridge and thereby determining the wetting progress.

At the same time the processor may advantageously be configured for determining the quality of the wetting e.g. by determining one or more validity parameters such as detecting if the wetting is complete in the entire width of the porous test strip, if a section of the porous test strip has been by-passed, if a section or a part of the porous test strip has been flooded by the liquid sample, if the migration along the porous test strip has been inhomogeneous or uneven and/or other features that might influence the validity of the test run. The computer system may comprise a threshold for each of one or more of the validity parameters and the processor may determine if one or more validity parameters does not fulfil the threshold.

In an embodiment the processor is configured for selecting a subgroup of pixels of each of one or more of the rows of W pixels which subgroup of pixels is referred to as 'W pixels. The subgroup of 'W pixels is advantageously selected to correspond to the width of the porous test strip at the exposed zone, i.e. the 'W pixels comprise pixels that are arranged to collect photons reflected from the porous test strip at the exposed zone. For even higher accuracy a number of W pixels of a row corresponding to an area adjacent to the edge of the porous test strip at the exposed zone (i.e. arranged for collecting photons reflected from the area adjacent to the edge of the porous test strip at the exposed zone) may be excluded from the subgroup of 'W pixels.

In the same way the processor may be configured for selecting a subgroup of pixels of each of one or more of the columns of L pixels which subgroup of pixels is referred to as 'L pixels. The subgroup of 'L pixels is advantageously selected to correspond to the length of the porous test strip at the exposed zone, i.e. the 'L pixels of a column W pixels comprise pixels that are arranged to collect photons reflected from the porous test strip at the exposed zone. For even higher accuracy a number of L pixels of a column corresponding to an area adjacent to the top or bottom edge of the porous test strip at the exposed zone (i.e. arranged for collecting photons reflected from the area adjacent to the top or bottom edge of the porous test strip at the exposed zone) may be excluded from the subgroup of 'L pixels.

In an embodiment the processor is configured for determining a porous zone pixel array comprising a sub array of the columns of L pixels aligned with the length of the strip and rows of W pixels aligned with the width of the strip, the porous zone pixel array comprises columns of L' pixels aligned with the length of the strip and rows of W' pixels aligned with the width of the strip.

In an embodiment the porous zone pixel array comprises substantially all the pixels that are arranged for collecting photons reflected from the porous test strip in the exposed zone.

In an embodiment the porous zone pixel array comprises only some of the pixels that are arranged for collecting photons reflected from the porous test strip in the exposed zone, such as from about 10% to 99%, such as from about 20% to about 90%, such as from about 30% to about 80% of the pixels that are arranged for collecting photons reflected from the porous test strip.

Advantageously the porous zone pixel array comprises less than 10%, preferably less than 5%, more preferably less than 2% of pixels that are not arranged for collecting photons reflected from the porous test strip.

In an embodiment the processor is configured for determining at least a plurality of rows of W' pixels of the porous zone pixel array from at least one set of pixel data. Preferably the processor is configured for determining at least 50%, such as at least 80%, such as substantially the entire porous zone pixel array from at least one set of pixel data.

By programming the processor to determine the porous zone pixel array and to perform the comparison of pixel values for determining the wetting progress and/or wetting parameters as disclosed above, the resulting validation and/or determination may be even more accurate and may be determined even faster.

In an embodiment the processor is configured for determining the porous zone pixel array from 2 or more sets of pixel data, such as at least 5 sets of pixel data, such as from 8 to 50 sets of pixel data, such as from 10 to 25 sets of pixel data of a series of frames.

In an embodiment the processor is configured for determining the porous zone pixel array from one single set of pixel data.

In an embodiment the at least one set of pixel data for performing one or more determinations comprises a pixel data set of an image acquired prior to wetting the sampling zone or prior to fully wetting the porous strip.

In an embodiment the at least one set of pixel data for performing one or more determinations comprises a pixel data set of an image acquired after the porous strip in the exposed zone has been fully wetted.

In an embodiment the processor is configured for determining the porous zone pixel array by a configuration comprising determining an average or a mean row W pixel value and determining pixels of the W row that has pixels values above or below a preselected threshold relative to the average or mean row W pixel value. The preselected threshold may be acquired from a user and/or stored by the computer system. The threshold may e.g. be that the processor is configured for determining pixels of the W row that has pixels of at least 10% above or below the row W pixel value, such as determining pixels that have pixel values of at least 25% above or below the row W pixel value, such as at least 25%, such as at least 50%, such as at least 100%, such as at least 200% above or below the average or mean row W pixel value.

The term "row W pixel value" means the average or mean row W pixel value unless otherwise specified.

Where the porous test strip reflects a lower intensity of the light waves that are used for the intensity value than the material of the lateral flow cartridge housing surrounding the reading window, the processor will determine values below the threshold and visa verse. Where the material of the lateral flow cartridge housing surrounding the reading window has different areas with different reflection properties an average of these is used to select the threshold.

In an embodiment the processor is configured for comparing pixel values of a W pixel row with the row W pixel value of that row, for repeating this process for a plurality of W pixel rows and determining pixels of the respective W pixel row that have pixels values above or below the respective row W pixel value, for example determining pixels of the W pixel rows that have pixels values of at least 10% above or below the respective row W pixel values.

In an embodiment the processor is configured for determining first and last pixels of each of the plurality of W pixel rows which have a pixel value above or below the preselected threshold. Advantageously the processor is further configured for determining at least the plurality of rows of W' pixels of the porous zone pixel array based on the positions of the determined first and last pixels of each of the plurality of W pixel rows. The processor may e.g. be configured for determining at least 50%, such as at least 80%, such as substantially the entire porous zone pixel array.

In an embodiment the lateral flow cartridge comprises exposed zone fiducial mark and the processor is configured for determining the porous zone pixel array at least partly based on reflections from the exposed zone fiducial mark.

In an embodiment the lateral flow cartridge comprises an exposed zone fiducial mark having a reflectivity that differs by at least 100%, such as at least 200% from the reflectivity of the housing surrounding the exposed zone. The processor is advantageously configured for determining the pixels of the plurality of rows W pixels collecting photons reflected from the exposed zone fiducial mark and based on the positions of the determined pixels collecting photons reflected from the exposed zone fiducial mark, determining the porous zone pixel array.

By using a lateral flow cartridge having such an exposed zone fiducial mark the processor may determine the porous zone pixel array with a high accuracy irrespectively of the reflections of the porous test strip. Where the computer system comprises data representing the distance between the exposed zone fiducial mark and the exposed zone, the porous zone pixel array can be determined very fast using a relatively low amount of computer power.

The exposed zone fiducial mark and the above described alignment mark may be the same or different marks.

In an embodiment the processor is configured for determining the porous zone pixel array by a configuration comprising determining an average or a mean column L pixel value and determining pixels of the L pixel column that have pixels values above or below a preselected threshold as described above for the determination of the row W pixel value.

In an embodiment the threshold may be that the processor is configured for determining pixels of the column that have pixels of at least 10% above or below the column L pixel value, such as determining pixels that have pixel values of at least 25% above or below the row W pixel value, such as at least 25%, such as at least 50%, such as at least 100%, such as at least 200% above or below the average or mean column L pixel value.

The term "column L pixel value" means the average or mean column L pixel value unless otherwise specified.

Where the porous test strip reflects a lower intensity of the light waves that are used for the intensity value than the material of the lateral flow cartridge housing surrounding the reading window, the processor will determine values below the threshold and visa verse. Where the material of the lateral flow cartridge housing surrounding the reading window has different areas with different reflection properties an average of these is used to select the threshold.

In an embodiment the processor is configured for comparing pixel values of a L pixel column with the column L pixel value of that column, for repeating this process for a plurality of L pixel column and determining pixels of the respective L pixel column that have pixels values above or below the respective column L pixel value, for example determining pixels of the L pixel columns that have pixels values of at least 10% above or below the respective column L pixel values.

In an embodiment the processor is configured for determining first and last pixels of each of the plurality of L pixel column which has a pixel value above or below the threshold relative to the column L pixel value and based on the positions of the determined first and last pixels of each of the plurality of L pixel column, determining at least the plurality of rows of L' pixels of the porous zone pixel array, preferably determining at least 50%, such as at least 80%, such as substantially the entire porous zone pixel array.

In an embodiment the lateral flow cartridge comprises an exposed zone fiducial mark having a reflectivity that differs by at least 100%, such as at least 200% from the reflectivity of the housing surrounding the exposed zone and the processor is configured for determining the pixels of the plurality of columns of L pixels collecting photons reflected from the exposed zone fiducial mark and based on the positions of the determined pixels collecting photons reflected from the exposed zone fiducial mark, determining the porous zone pixel array.

In an embodiment the processor is configured for deriving a derived row W' pixel value from each of a plurality of row W' pixel values. The derived row W' pixel value be derived by any mathematical method and preferably by methods that increase potential differences between respective row W' pixel values.

In an embodiment the processor is configured for deriving a derived row W' pixel value by determining a mean value of the row W' pixel values or by determining an average value of the row W' pixel value, optionally leaving out a number of pixel values of pixels closer to the edges of the porous zone pixel array.

In an embodiment the processor is configured for deriving a derived row W' pixel value by multiplying the values of the W' pixels with each other.

In an embodiment the processor is configured for deriving a derived row W' pixel value by weighting values of a number of W' pixels closer to the middle of the row higher than 'W pixels closet to the edges of the porous zone pixel array.

In an embodiment the processor is configured for, for one or more rows of W' pixels, comparing derived row W' pixel values of corresponding W' rows of a plurality of sets of pixel data, identifying derived row W' pixel values of corresponding W' rows that differ beyond a threshold from one set of pixel data to a next set of pixel data and for each identified derived row W' pixel value determining the time attribute of the next set of pixel data and preferably identifying the position of the row of W' pixels.

Thereby the lateral flow test system may determine with a very high accuracy the time where a selected area of the exposed zone of the porous test strip is wetted.

The derived row W' pixel values may be processed by comparing the average or mean row pixel value of the row of W aligned pixels as described above to perform the corresponding determinations of porous test strip wetting described above.

In an embodiment the processor is configured for, for each of a number $n_i$ to $n_j$ of rows of W' pixels, comparing derived row W' pixel values of corresponding W' rows of a plurality of sets of pixel data, identifying derived row W' pixel values of corresponding W' rows that differ beyond a threshold from one set of pixel data to a next set of pixel data and for each identified row W' pixel value determining the position of the row of W' pixels and optionally the time attribute of the next set of pixel data.

The i and j number of the $n_i$ to $n_j$ of rows of W' pixels may be selected by the user or be pre-programmed. Preferably j minus i is at least 5, preferably at least 10, more preferably at least 20. "i" may be 1 (the first row) or it may have a higher number such as 5 or 10.

Thereby the lateral flow test system may determine the wetting progress and/or the velocity (flow rate) of the wetting front.

The term "wetting front" means the front of the liquid sample as it migrates along the porous test strip in the exposed zone.

By processing the derived row W' pixel values of corresponding W' rows of a plurality of sets of pixel data, the lateral flow test system may be configured for determining the wetting progress and/or the velocity (flow rate) of the wetting front as well as determining one or more quality parameters of the wetting e.g. the flow rate as a function of the wetting front.

In an embodiment the processor is configured for processing the derived row W' pixel values of corresponding W' rows of a plurality of sets of pixel data to thereby determine the quality of the wetting e.g. by determining one or more validity parameters such as detecting if the wetting is complete in the entire width of the porous test strip, if a section of the porous test strip has been by-passed, if a section or a part of the porous test strip has been flooded by the liquid sample, if the migration along the porous test strip has been inhomogeneous or uneven and/or other features that might influence the validity of the test run. The computer system may comprise a threshold for each of one or more of the validity parameters and the processor may determine if one or more validity parameters does not fulfil the threshold.

In an embodiment the processor is configured for comparing derived row W' pixel values of each of the plurality of W' rows of a set of pixel data with each other to determine if the derived row W' pixel values differ from one row to a next row along the $n_i$ to $n_j$ rows of W' pixels. The processor is advantageously configured for repeating the processing for a next set of pixel data. Thereby the processor may determine the wetting progress and/or one or more of the above described quality parameters. In particular the processor may determine the position of the wetting front as a function of the time attribute of the respective sets of pixel data.

In an embodiment the processor is configured for subtracting a value of a set of pixel data from corresponding values of a previous or a next set of pixel data and determining pixel values and/or derived pixel values that have changed beyond a threshold.

In an embodiment the processor is configured for subtracting values of porous zone pixel array pixels of a set of pixel data from corresponding pixels of a previous or a next set of pixel data and determining pixel values and/or derived pixel values of the porous zone pixel array that have changed beyond a threshold.

The processor may advantageously be configured for deriving a derived row W' pixel value from each of a plurality of row W' pixel values and subtracting a set of pixel data from a previous or a next set of pixel data and determining derived row W' pixel values that have changed, and preferably the position of the pixel W' rows with changed derived row W' pixel values and the time attribute of the set of pixel data or of the next set of pixel data.

Thereby the processor may determine the wetting progress and/or wetting quality parameter with a high accuracy using relatively low computer processing power.

Due to the very fast processing the processing may be performed in real time and thus any faults or errors in the test run may immediately be discovered and the test run may optionally be terminated immediately, thereby saving time for the user.

In an embodiment the processor is configured for determining rows comprising pixel values that have changed beyond a threshold and determining the position of the pixel W' row(s) or pixel W row(s) comprising the pixel with changed pixel value and the time attribute of the set of pixel data or of the next set of pixel data.

In an embodiment the processor is configured for deriving a derived row W' pixel value or a derived row pixel W pixel value from the row comprising the pixels with changed pixel values. Thereby the processor need not use processing power on the rows of pixels where the values have not changed beyond the threshold.

As mentioned above the porous test strip usually comprises immobilized captures for capturing labelled particles or for capturing the target analyte which has been labelled, and wherein the label is optically detectable.

Advantageously the processor is configured for determining if a derived row W' pixel value or derived row pixel W pixel value represents a control mark, e.g. by revealing if a row W' pixel value differs beyond a threshold value from one or more other derived row W' pixel values.

In an embodiment the pixel value applied for determining the control mark where labelled particles have been captured is advantageously a value of intensities of light comprising wavelength of the label. Thus, where the label primarily comprises red light the value applied is advantageously a value representing the intensities of red light.

In an embodiment the processor is configured for determining if a derived row W' pixel value or a derived row pixel W pixel value represents a positive mark, e.g. by revealing if a row W' pixel value differs beyond a threshold value from one or more other derived row W' pixel values.

In an embodiment the pixel value applied for determining the positive mark where labelled analytes have been captured is advantageously a value of intensities of light comprising wavelength of the label. Thus where the label primarily comprises red light the value applied is advantageously a value representing the intensities of red light.

Generally, the lateral flow test system is very robust and insensitive to incident light in particular where the pixel values of respective sets of pixel data are subtracted thereby removing any potential influence of constant incident light.

However, in some situations it may be desired to compensate for incident light.

The processor may thus be configured for noise correcting the pixel values and/or pixel row values from noise caused by incident light. The noise correction may in an embodiment comprise that the processor is configured for averaging the pixel values of pixels of the row outside the porous zone pixel array to obtain a row pixel reference value and compensate the row pixel value with the row pixel reference value e.g. by determining a derived row pixel value as a relative row pixel value divided by the row pixel reference value and deeming the derived value to be the noise corrected row pixel value.

In an embodiment the illumination arrangement is configured for providing flash illumination. The flash rate of the flash illumination may preferably be coordinated with the frame rate, preferably such that the illumination arrangement is configured for emitting a flash timely coordinated with the acquisition of each image.

In an embodiment the processor is configured for discharging sets of pixel data of blurred images. The processor may be configured for discharging sets of pixel data of images that are blurred beyond a preselected threshold.

Algorithms for detecting blurred images are well known and may be applied. For example the detection of blurred image may be as described in the internet publication "Blur Detection for Digital Images Using Wavelet Transform" by Hanghang Tong et al. https://www.cs.cmu.edu/~htong/pdf/ICME04_tong.pdf Whereas the present disclosure is mainly described for lateral flow test systems where the lateral flow cartridge has only one test strip it should be understood that the lateral flow cartridge may have two or more porous test strips. The two or more porous test strips and their respective exposed zones may be arranged in any geometrical configuration. Advantageously the two or more porous test strips are arranged to be parallel or with an angle to each other of up to 45 degrees, such as up to 30 degrees. The main point is that the exposed zones are within the field of view of the camera. Alternatively the lateral flow test system may have two or more cameras.

Where the two or more exposed zones or respective porous test strips are within the field of the camera—which is generally preferred—the processor is configured for sectioning each image into sections comprising images of the respective exposed zone and processing the images and the sets of pixel data of the respective image as described above. Images of two or more exposed zones are referred to as group-image. Pixel data of such group images are referred to as group sets of pixel data.

In an embodiment the lateral flow cartridge comprises two or more test strips and the cartridge comprises at least one reading window into each of the respective porous test strips at its distal portion exposing at least an exposed zone of the respective porous strips. Each exposed zone has a length and a width. Each of the two or more porous strips has a sampling zone, which may be a common sampling zone or individual sampling zones. The video camera is configured for acquiring the series of digital group images comprising each of the exposed zones. The reader e.g. the camera, is configured for transmitting each group image as a group set of pixel data. The processor is configured for receiving and storing the group sets of pixel data of the plurality of consecutive digital images and for dividing the group sets of pixel data into sets of pixel data representing image of the respective exposed zones.

In an embodiment the group sets of pixel data each comprise a group pixel sensor array and the processor is configured for defining group columns of L pixels and group rows of W pixels of the group pixel sensor array of a set of group pixel data and for dividing the group columns of L pixels and group rows of W pixels into pixel sensor arrays associated to each of the respective porous strips providing that each pixel sensor array comprises columns of L pixels aligned with the length of the strip and rows of W pixels aligned with the width of the strip. Thereby the group sets of pixel data may be divided into sets of pixel data representing image of the respective exposed zones.

In an embodiment the processor is preprogrammed to segmenting the image and to divide the group sets of pixel data into predefined sets of pixel data.

In an embodiment the lateral flow cartridge comprises a dividing fiducial mark which may be optically detected by the camera and the processor may determine the dividing fiducial mark and use this for dividing the group sets of pixel data into sets of pixel data.

All features of the present disclosure including ranges and preferred ranges can be combined in various ways within the scope of the present disclosure, unless there are specific reasons not to combine such features.

The lateral flow test system shown in FIG. 1 comprises an optical reader 1 with a reader housing, a not shown lateral flow cartridge and a computer system 3. The optical reader 1 comprises a slot 2 for inserting the lateral flow cartridge and encased in its housing it comprises a not shown video camera adapted for acquiring a series of digital images of an exposed zone of the cartridge when inserted into the slot 2 and transmitting sets of pixel data representing the acquired images preferably in real time streaming to the computer system 3. The computer system 3 is in this embodiment external to the reader housing and comprises a screen 3a for displaying the determinations of the test results in real time for a user.

The lateral flow test system shown in FIG. 2 comprises an optical reader 11 with a reader housing 11a, a lateral flow cartridge 17 and a computer system 13. The optical reader 11 comprises a slot and support elements 16a, 16b. The lateral flow cartridge 17 is inserted into the slot and held in a fixed position by the support elements 16a, 16b. The optical reader 11 comprises a video camera 14 and an illumination arrangement 15. The illumination arrangement 15 is adapted for illuminating a not shown exposed zone of the porous strip of the lateral flow cartridge 17 and the video camera 14 is configured for acquiring a series of digital images comprising the exposed zone of the porous strip and for transmitting each digital image as a set of pixel data to the computer system 13. The reader system further comprises electronics 18 for operating the camera 14 and the illumination arrangement 15. The electronics 18 is preferably controlled by the computer system 13. In the shown embodiment the computer system 13 is located inside the housing 11a of the optical reader 11. The computer system is in wireless data communication with an external computer 13a, such as a pc, for receiving instructions via an interface at the external computer and for transmitting determinations of the test results in real time for being displaced on the screen 13b for a user.

The porous test strip shown in FIG. 3a is a typical test strip for a lateral flow cartridge.

The porous test strip comprises from its proximal end towards its distal end a sampling pad 21 arranged to be at the sampling zone, a conjugate pad 22 with the labelled particles, a porous membrane 23 (e.g. of nitrocellulose) carrying a test zone 25 and a control zone 24 and a fluid sink comprising an adsorbent pad 26. All the pads and membrane may advantageously be supported by a not shown backing. The various zones and pads may be as described above.

In the embodiment of a porous test strip shown in FIG. 3b, the porous test strip differs from the porous test strip of FIG. 3a in that the test zone 25a and a control zone 24a are positioned such that when the test is positive and optically labelled molecules/particles are captured in both zones, the zones will show a cross, whereas when the test is negative or the control zone is not activated a line (minus) or nothing will be shown in the zones.

The lateral flow cartridge shown in FIG. 4a comprises a housing 31a encasing a porous test strip, an inlet opening 32a to a sampling zone and a reading window 33a into the porous test strip at its distal portion exposing an exposed zone of the porous strip. The porous test strip may e.g. be as shown in FIG. 3a or 3b. The dotted circle 34 illustrates a field of view of the video camera. The field of view is adapted to comprise the exposed zone and preferably the field of view is somewhat larger since the reading window or the cartridge may vary.

The lateral flow cartridge shown in FIG. 4b comprises a housing 31b encasing 3 porous test strips each arranged to have an exposed zone in the respective reading windows 33b, 33b' and 33b". The housing 31b comprises three inlet openings 32b, 32b' and 32b" into the sampling zones of the respective porous test strips. In this embodiment the porous test strips are arranged substantially parallel.

The lateral flow cartridge shown in FIG. 4c comprises a housing 31c encasing 3 porous test strips each arranged to have an exposed zone in the respective reading windows 33c, 33c' and 33c". The housing 31b comprises one common inlet opening 32c' into the sampling zones of the respective porous test strips. In this embodiment the porous test strips are arranged with an angle to each other. The dotted field 34c illustrates a field of view of the video camera for acquiring a series of group images. The dotted lines 35 illustrate segmenting lines for segmenting the images as described above.

The lateral flow cartridges of FIG. 4a, 4b or 4c mat comprise one or more fiducial marks as described above.

FIG. 5 shows average values of column as a function of the position of the column along the horizontal position. The line 41 illustrates the average value of all of the pixel columns. The dotted line 42 illustrates the mean value (cut off mean) of the pixel columns. The curve 43 shows the average values of column minus the cut of mean as a function of the horizontal position of the pixel column. It can be seen that the edges of the exposed zone of the porous test strip are clearly identified.

FIG. 6 shows a plot of determined row 'W pixel value changes from respective sets of pixel data where the pixel values of the previous set of pixel data have been subtracted from the pixel values of these respective sets of pixel data.

It should be noted that dry nitrocellulose which was used for the porous test strip in this example is more reflective than wet nitrocellulose. Thus, as the porous test strip of nitrocellulose is wetted the reflection will decrease.

Each curve 51, 52, 53 is obtained from values of sets of pixel data where the values of the previous sets of pixel data have been subtracted. The resulting values of the row with the lowest value (which will be negative) have been averaged to obtain a row 'W pixel value changes from the sets of pixel data and this has been repeated for all of the sets of pixel data. Only some of the row 'W pixel value changes have been plotted, namely the 6 first row 'W pixel value changes 51 and the row 'W pixel value changes which reveal the control mark 52 and the test mark 53.

It can be seen that the bottom points of each of the row 'W pixel value changes indicating the wetting front are on the same level which is a clear indication that the porous test strip has been wetted in its entire width.

FIG. 7 is another plot of determined row 'W pixel value changes from respective sets of pixel data where the pixel values of the previous set of pixel data have been subtracted from the pixel values of these respective sets of pixel data. Here the bottom points of each of the row 'W pixel value changes 51a, 51b indicating the wetting front are not on the same level. It can be seen that the value of some of the row 'W pixel value changes 51b is significantly higher than other of the row 'W pixel value changes 51a. This indicates that a section of the porous test strip is not fully wetted but has been at least partly by-passed and that the test run therefore is not valid. Also it can be seen that the test mark is not found.

FIG. 8 is a plot of an example of a determined flow rate as a function of the length position of the porous test strip in the exposed zone. It can be seen that the flow rate is slightly decreasing along the length of the porous test strip. For some test strips this may be acceptable in particular where the test strip is relatively long. For other porous test strips the decreasing flow rate may indicate that the amount of liquid sample applied to the sampling zone is insufficient.

FIG. 9 shows a plot of another example of a determined flow rate as a function of the length position of the porous test strip in the exposed zone. Here it can be seen that the flow rate appears to decrease drastically after a first length of the porous test strip where after it becomes substantially constant. This may indicate that too much liquid sample has been applied to the sampling zone resulting in a flooding of the first length of the porous test strip.

FIG. 10 shows a plot of yet another example of a determined flow rate as a function of the length position of the porous test strip in the exposed zone. Here it can be seen that the flow rate at a length position of the porous test strip suddenly drops and there after rises to normal again. This may indicate that the porous test strip may be damaged at the indicated position.

The process diagram shown in FIG. 11 illustrates an example of a series of processes steps which an embodiment of the lateral flow test system may be configured for performing.

The first step in the series of steps listed in the process diagram comprises that the computer system receives set n of pixel data associated to the time attribute t'n. "n" means a number which is an integer, which may be "1" to indicate the first set of pixel data or it may be a higher integer, such as 2, 3 or higher. The set of pixel data with the number n is here designated as the set of pixel data used for determining the porous zone pixel array L',W'. When this is determined, the relative orientation between the video camera and the porous test strip in the exposed zone will be known to the computer system and the determination of the porous zone pixel array L', W' for the n set of pixel data may be applied for all the sets of pixel data for the respective series of images.

As mentioned in the process diagram the processor of the computer system is programmed for determining the relative orientation between the video camera and the porous test strip, for defining columns of L pixels and rows of W pixels and for processing values of a number of rows of W pixels by a method comprising determining a first and a last pixel of each row that has a value that differs from the respective row W value (average or mean) beyond a threshold, determining the best fit of pixels aligned along a border along said respectively first and last pixel and determining of the porous zone pixel array L',W' as described above.

The steps described above are an example of the programming of the computer system for determining the porous zone pixel array L', W'.

The next steps in the process diagram of FIG. 11 comprise that the processor is configured for deriving a derived row value of at least one of the X' row of pixel data of one set of pixel data and for a next set of pixel data and for comparing changes between corresponding rows to find the wetting front and the time of wetting.

In the example the processor performs this step on the set n of pixel data and the set n+1 of pixel data. It should be understood that the processor may perform this process on any of the sets of pixel data, preferably of images which have time attributes which are very close, preferably of set of pixel data of subsequent images.

By comparing derived row W' pixel values from corresponding rows with respective time attributes t'n and t'n+1 and identifying changes beyond threshold, the computer system may identify the position of a change in value as the wetting front and the time attribute may indicate the time that the wetting has reached this position.

By repeating this processing for the set of pixel data of the consecutive images of the series the processor may determine the wetting rate as a function of the positon of the wetting front and as seen in the example above the computer system may further determine if the porous test strip is correctly wetted or if an error has occurred.

The process diagram of FIG. 12 illustrates an example of a series of processes steps which an embodiment of the lateral flow test system may be configured for performing and which process is based on withdrawing pixel values from one image from pixel values of a subsequent image before determining derived row values.

The process illustrated in FIG. 12 comprises receiving a set n of pixel data associated to the time attribute t'n, receiving a subsequent set n+1 of pixel data acquired at time t'n+1 and subtracting the n set op pixel data from the n+1 set of pixel data and thereby identifying changed pixels with time attribute t'n+1 changes with time attribute t'n+1.

The processor is configured for thereafter identifying row(s) with pixels having changed pixel value beyond a threshold and optionally for determining the row W' pixel (or W pixel) value from the identified row.

Based on the row with changed pixels or the row W' pixel value thereof the processor may be configured for identifying the row position of changed pixels or rows of changed pixels as the wetting front and identifying time attribute t'n+1 as time of wetting at the row position.

The invention claimed is:

1. A lateral flow test system comprising an optical reader, a lateral flow cartridge and a computer system, the lateral flow cartridge having a proximal portion and a distal portion and comprising a porous test strip a sampling zone, a strip length and a cartridge housing supporting said porous test strip, wherein said cartridge housing has an inlet opening for applying liquid to the sampling zone and at least one reading window into the porous test strip at its distal portion exposing at least an exposed zone of said porous test strip, having a length and a width, said exposed zone having at least a portion distally to the sampling zone;

wherein said optical reader comprises a reader housing and a slot for inserting at least the distal portion of the cartridge into said reader housing, said optical reader further having an illumination arrangement configured to illuminate said at least one exposed zone of said porous strip when said cartridge is inserted into the slot of the reader housing and a video camera configured for acquiring a series of digital images comprising said exposed zone of said porous strip, wherein the optical reader is configured for transmitting each digital image as a set of pixel data;

wherein said computer system comprises a storing medium and a processor, said processor being configured for receiving said sets of pixel data representing said plurality of consecutive digital images and for calculating wetting progress along the length of said exposed zone of said porous strip based on changes of light reflection from the consecutive digital images;

wherein the video camera comprises a pixel sensor array having a two-dimensional array of pixels;

wherein the video camera comprises a pixel array comprising rows and columns (N×M) of pixels, said pixel array having a fill factor of at least about 50%;

wherein said video camera is arranged such that its rows and columns of pixels are aligned with respectively the width and the length of the porous strip thereby defining columns of L pixels and rows of W pixels;

wherein said processor is configured to define columns of L pixels and rows of W pixels of said pixel sensor array, by a method comprising comparing pixel values of a set of pixel data and determining the orientation of the porous strip and defining columns of L pixels aligned with the length of the strip and rows of W pixels aligned with the width of the strip;

wherein said processor compares pixel values of at least one L,W pixel of two or more sets of pixel data of the consecutive digital images to determine the time that light reflection is changing at a position of said porous test strip, corresponding to the L,W pixel, due to wetting;

wherein the processor is configured to compare pixel values of a set of pixel data by a method comprising for each of a plurality of camera pixel rows determining an average or a mean camera row pixel value and determining pixels that have pixels values of at least 10% above or below the camera row pixel value; and wherein the lateral flow cartridge comprises an alignment fiducial mark having a reflectivity that differs by at least 10% from the reflectivity of the housing surrounding the exposed zone, said processor being configured for determining the pixels of the plurality of camera pixel rows collecting photons reflected from said alignment fiducial mark and based on the positions of the determined pixels collecting photons reflected from said alignment fiducial mark, determining the orientation of the porous strip.

2. The system of claim 1, wherein the video camera is a webcam operating with a frame rate of at least about 0.1 Hz.

3. The system of claim 1, wherein the processor is configured to determine first and last pixels of each of the plurality of camera pixel rows which have pixels values of at least 10% above or below the respective average or mean camera row pixel value and based on the positions of the determined first and last pixels of each of the plurality of camera pixel rows, determining the orientation of the porous strip.

4. The system of claim 1, wherein each set of pixel data is associated with a time attribute representing a time of acquisition of said respective image of said series of images.

5. The system of claim 4, wherein the processor is configured to compare pixel values of at least one L, W pixel for a plurality of sets of pixel data of said series of digital images to determine the time attribute of a set of pixel data where the L, W pixel value data differs relative to L,W pixel values of corresponding pixels from previous or subsequent sets of pixel data.

6. The system of claim 1, wherein the processor is configured to determine a porous zone pixel array comprising a sub array of the columns of L pixels aligned with the length of the strip and rows of W pixels aligned with the width of the strip, said porous zone pixel array comprises columns of L' pixels aligned with the length of the strip and rows of W' pixels aligned with the width of the strip.

7. The system of claim 6, wherein the processor is configured to determine at least a plurality of rows of W' pixels of the porous zone pixel array from at least one set of pixel data.

8. The system of claim 7, wherein the processor is configured to determine the porous zone pixel array from two or more sets of pixel data of a series of frames.

9. The system of claim 7, wherein the processor is configured to determine the porous zone pixel array from one single set of pixel data.

10. The system of claim 7, wherein the at least one set of pixel data comprises a pixel data set of an image acquired prior to wetting the sampling zone or prior to fully wetting the porous strip.

11. The system of any one of claim 7, wherein the at least one set of pixel data comprises a pixel data set of an image acquired after the porous strip in the exposed zone has been fully wetted.

12. The system of claim 1, wherein the processor is configured for noise correcting the pixel values and/or pixel row values from noise caused by incident light, the noise correction comprising that the processor is configured for averaging the pixel values of pixels of the row outside the porous zone pixel array to obtain a row pixel reference value and compensating the row pixel value with said row pixel reference value by determining a derived row pixel value as a relative row pixel value/row pixel reference value and deeming the derived value to be the noise corrected row pixel value.

13. The system of claim 1, wherein the illumination arrangement is configured for flash illumination, said flash illumination having a flashing rate which is coordinated with the frame rate such that the illumination arrangement is configured for emitting a flash timely coordinated with the acquisition of each image.

14. The system of claim 1, wherein the processor is configured to discharge sets of pixel data of blurred images.

15. The system of claim 1, wherein the lateral flow cartridge comprises two or more test strips, the cartridge comprises at least one reading window into each of the respective porous test strips at its distal portion exposing at least an exposed zone of said respective porous strips, each exposed zones having a length and a width, each of said two or more porous strips has a sampling zone, which is one of a common sampling zone and individual sampling zones, said video camera is configured for acquiring said series of digital group images comprising each of said exposed zones and, wherein the reader is configured to transmit each group image as a group set of pixel data, said processor being configured to receive and store said group sets of pixel data of said plurality of consecutive digital images and to divide the group sets of pixel data into sets of pixel data representing images of the respective exposed zones.

16. The system of claim 15, wherein said group sets of pixel data each comprise a group pixel sensor array, said processor being configured to define group columns of L pixels and group rows of W pixels of said group pixel sensor array of a set of group pixel data and to divide said group columns of L pixels and group rows of W pixels into pixel sensor arrays associated to each of said respective porous strips, each pixel sensor array comprises columns of L pixels aligned with the length of the strip and rows of W pixels aligned with the width of the strip.

* * * * *